United States Patent [19]

Hashimoto et al.

[11] 4,035,173

[45] July 12, 1977

[54] SELECTIVELY THINNING AND FERTILIZING TIMBER FORESTS

[75] Inventors: Saburo Hashimoto, Yorba Linda; Donald C Young, Fullerton, both of Calif.

[73] Assignee: Union Oil Company of California, Brea, Calif.

[21] Appl. No.: 673,792

[22] Filed: Apr. 5, 1976

Related U.S. Application Data

[63] Continuation-in-part of Ser. No. 560,638, March 21, 1975, abandoned.

[51] Int. Cl.$^2$ .................... C05C 9/00; C05C 1/00
[52] U.S. Cl. ........................ 71/30; 71/28; 71/64 C; 71/1; 47/DIG. 13
[58] Field of Search ............ 71/1, 27–30, 71/64 C; 47/DIG. 13

[56] References Cited

U.S. PATENT DOCUMENTS

| | | | |
|---|---|---|---|
| 2,869,996 | 1/1959 | Vierling | 71/29 |
| 2,978,309 | 4/1961 | Buc | 71/1 |
| 3,046,105 | 7/1962 | Young | 71/51 |
| 3,539,325 | 11/1970 | Young et al. | 71/1 |
| 3,558,300 | 1/1971 | Wagner | 71/1 |
| 3,640,698 | 2/1972 | Backlund | 71/1 X |
| 3,663,197 | 5/1972 | Backlund | 71/1 X |

FOREIGN PATENT DOCUMENTS

| | | | |
|---|---|---|---|
| 615,958 | 3/1961 | Canada | 71/30 |

OTHER PUBLICATIONS

Feeding Plants with Foliage Sprays, Beattie Horticulture, vol. XXXI, May, 1953, pp. 1209–1217.

*Primary Examiner*—Frank A. Spear, Jr.
*Assistant Examiner*—Ferris H. Lander
*Attorney, Agent, or Firm*—Richard C. Hartman; Dean Sandford; Michael H. Laird

[57] ABSTRACT

This invention relates to a method for simultaneously fertilizing and thinning commercial timber forests of which, as a general rule, the predominant population are conifers of the family Pinaceae. The trees are characterized in two groups, preferred and unpreferred, the preferred trees comprising one or more species of the conifer family Pinaceae while the unpreferred trees comprise either competing broadleaf varieties or species of the family Pinaceae which are less desirable in a given instance. Broadleaf brush and weeds can also be selectively eliminated by this procedure.

Selective thinning and fertilization is accomplished by applying to the foliage of all of the trees, brush and weeds an aqueous nitrogenous fertilizer solution containing an amount of a nitrogen source corresponding to at least about 12.5 weight percent elemental nitrogen at a dosage level sufficient to kill a substantial proportion of the unpreferred trees and/or brush by promoting extreme foliage burning and desiccation, yet insufficient to kill a substantial number of the preferred species which, by definition, are stronger and more tolerant to these solutions.

11 Claims, 2 Drawing Figures

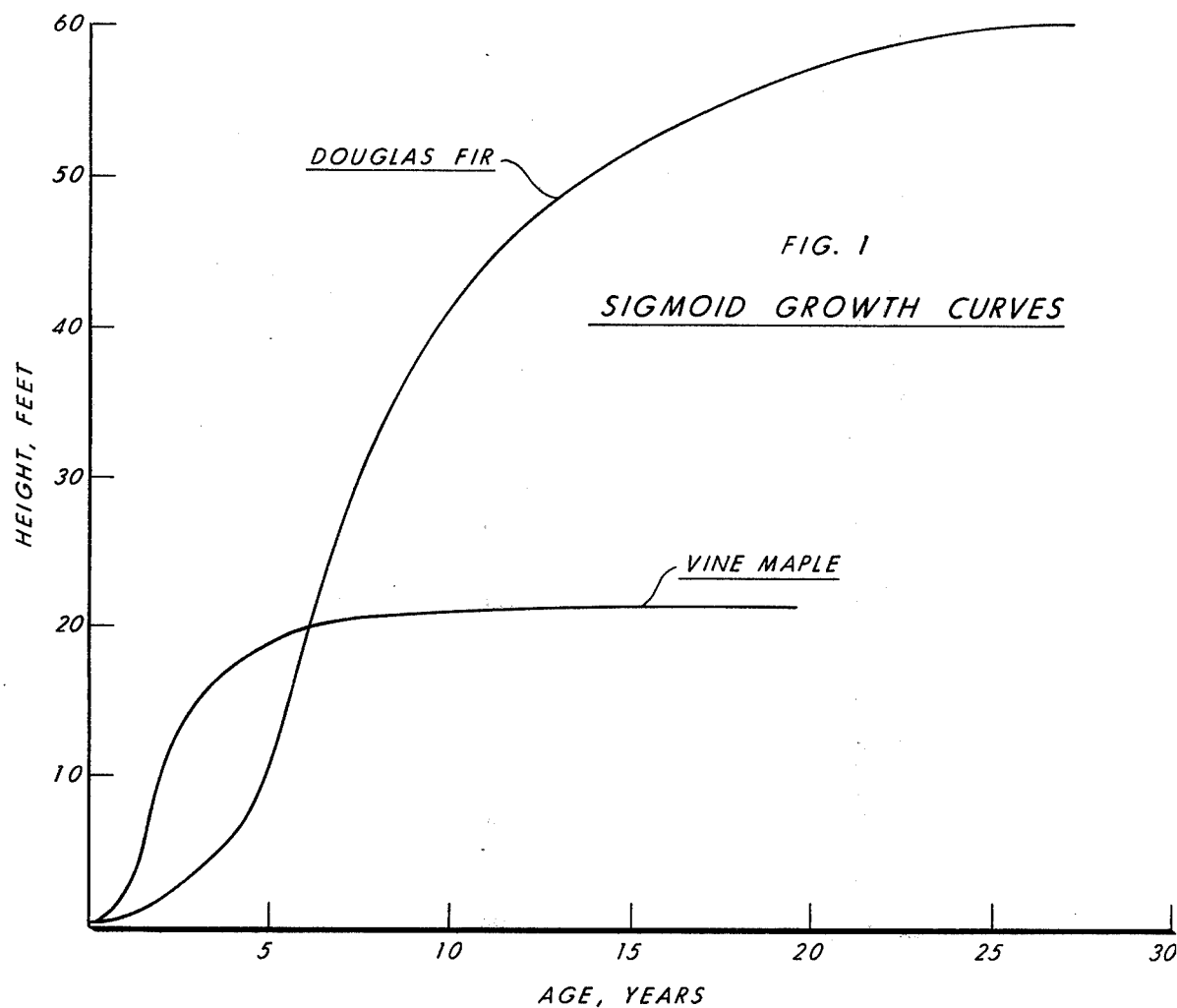

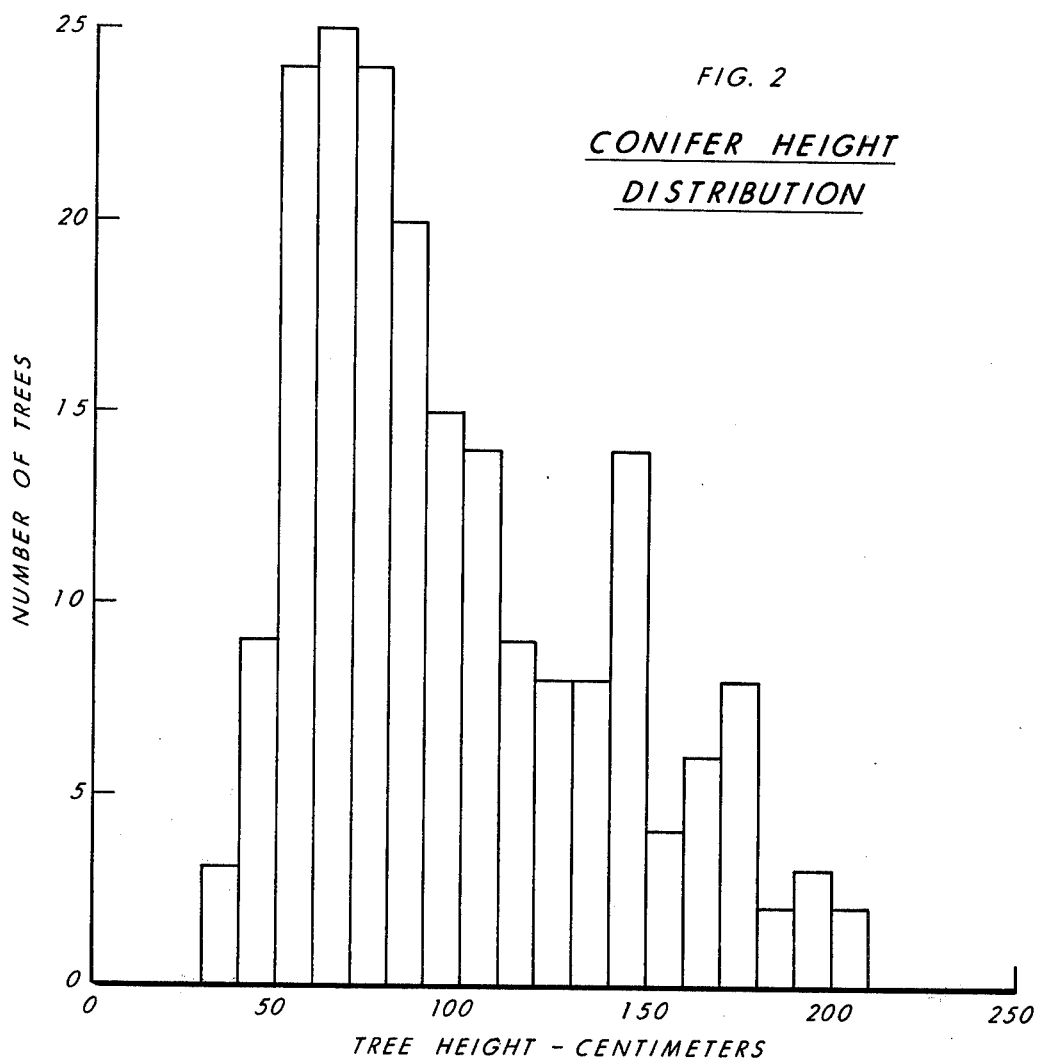

SELECTIVELY THINNING AND FERTILIZING TIMBER FORESTS

REFERENCE TO RELATED APPLICATIONS

This is a continuation-in-part of Ser. No. 560,638, filed Mar. 21, 1975, now abandoned.

BACKGROUND OF THE INVENTION

Methods of superior forest management are in ever greater demand due to the continuously rising demands for timber and other wood products. Increased forest growth and timber yield can be accomplished by selective thinning of over-populated forest stands, by eliminating competing species which are less desired in a particular instance, by fertilization, and optimally by a combination of all of these. Selective thinning has long been practiced either with herbicides or by actually mechanically destroying the unpreferred trees. These methods were obviously tedious, time-consuming and very expensive. Yet they are sufficiently productive to justify their use. Mechanical thinning is sometimes practiced even as late as 15 years after planting. Even during the initial growth stages, i.e., at 3 years of age, mechanical thinning involves substantial costs on the order of $100 to more than $500 per acre. Yet the United States Forest Service has established that ultimate wood production can be increased as much by selective thinning of members of the same species as can be obtained by fertilization. The effect on productivity is substantial.

Within the context of this invention, the term "preferred trees" includes species of the family Pinaceae which are more resistant to this treatment than are other "unpreferred" species. Thus, the unpreferred trees are the weaker members of the same species of Pinaceae. Only the most tolerant trees will survive. Hence, this procedure obviously can not be used to selectively eliminate conifers such as Douglas fir from a preferred broadleaf stand. Nevertheless, it can be used profitably in a large segment of the timber industry.

As a general rule, young forests and particularly replanted forests are considerably overstocked even with the desired tree species. It is also very difficult if not impossible to prevent the natural seeding of substantial numbers of non-preferred species, either conifers, broadleaf trees, brush or weeds. Thus in the usual course of forest development there are two competing factors that influence the growth rate of the preferred tree species and ultimate timber yield. These factors include competition between unpreferred broadleaf trees with the preferred species of the pine family, as well as competition between members of the same species which arises from original overstocking in both uncontrolled and replanted forest stands. Thus the members of the preferred species which will ultimately survive and constitute essentially the complete timber crop of the area must originally compete for sunlight, water, nutrients and growing space with unpreferred broadleaf trees or other species of the same family as well as with members of the same tree species.

The elimination of this competition for nutrients, sunlight, water, etc., during initial growth stage that is a principal objective of forest thinning. The advantages of faster growth and greater ultimate yield were considered sufficient to justify the tedious and expensive procedures previously employed. We have now discovered that these advantages can be achieved much less expensively by a simplified procedure which accomplishes not only the objective of forest thinning but simultaneously fertilizes and thereby accelerates the growth of the more vigorous members of the desired species.

It is therefore an object of this invention to provide an improved method for simultaneously fertilizing and selectively thinning forest trees.

Another object is the provision of a method for selectively eliminating unpreferred tree species and/or unpreferred members of the same tree species from overpopulated forest stands in the earlier stages of forest development.

Therefore, in accordance with one embodiment of this invention, forests comprising preferred commercial timber trees of the family Pinaceae as well as unpreferred trees of the same species, a second species of the family Pinaceae or broadleaf varieties having a lower tolerance to the aqueous nitrogenous fertilizer employed in this method than do the preferred trees, are selectively thinned and fertilized simultaneously by applying to the foliage of all of the trees an aqueous solution of a water soluble nitrogen source having a concentration corresponding to at least about 12.5 weight percent elemental nitrogen at a total elemental nitrogen dosage level sufficient to kill a significant proportion of the unpreferred trees.

The timber trees of greatest commercial significance are generally selected from the family Pinaceae, commonly known as the pine family, including seven genera, each of which encompasses numerous species. The generic classes within the pine family which constitute the principal commercial timber and wood byproduct crops are the Abies including all of the true firs such as Pony fir, Grand fir, Red fir, etc.; Picea including numerous species of spruce; Pinus including many species of pine such as loblolly, ponderosa, lodgepole, white pine, etc.; Pseudotsuga or false hemlock, the Douglas fir being a member of this genus rather than a true fir; and the genus Tsuga including numerous species of hemlock. The remaining two pine family genera, while generally being of lesser commercial importance within the context of this invention, are still suitable subjects for the application of this method. These include the genus Cedrus encompassing all species of cedar and the genus Larix encompassing the tamaracks.

We have discovered that all of these generic classes, and for that matter all species within each genus, have varied degrees of tolerance for the foliar application of the described solutions. The significant aspect of this tolerance is believed to be the degree of foliar damage promoted by a given amount of a specific solution having a given nitrogen content. The higher the burn level, the greater the immediate growth deterrent effect. The degree of discrimination achived — the relative advantage given the hardier trees — is the result of a balance between the deterrent effect on less tolerant trees and the fertilization effect on the preferred trees.

Variations in tolerance are also apparent between the numerous species of broadleaf trees commonly found in forested areas. Each broadleaf species has a different tolerance to these solutions. However, we observed that the broadleaf trees generally have a much lower tolerance than members of the pine family. This difference is sufficiently broad in fact that dosage levels of a given solution that will completely eradicate the broadleaf trees will serve only to fertilize and thereby promote the growth of the preferred trees of the Pinaceae family. Nitrogen compounds, solution concentrations and total dosage levels can be selected such that the broadleaf varieties are completely eliminated due to excessive desiccation while the preferred species suffer, at most, only nominal foliar burn.

We have also discovered that an even narrower line of discrimination can be observed and maintained between stronger and weaker members of the same tree species. For instance, as mentioned above, it is often the case that areas which are naturally or synthetically reforested are generally over-populated with the result that, even in the absence of competing species, members of the same preferred species must compete with each other for available sunlight, water, nutrients and growing space. Due to natural genetic differences, some members of the over-populated group are hardier, grow faster and are more able to tolerate adverse growing conditions. For one or more of these reasons, the hardier members will ultimately survive and kill off the less hardy members of the original population.

As is the case with any other population or group of species, the variance in the ability of the members of the group to survive is generally represented by a statistical distribution similar to a normal or Gaussian distribution. A few members of the group will be able to survive extreme conditions while a few will die off fairly early in the game. The greatest percentage of the population will fall somewhere between these two extremes. Nevertheless, the members of the group which also survive are inhibited in growth rate during the additional stages of their growth due to competition with the members of the class which ultimately do not survive. The elimination of such competition between members of the same species during the early stages of forest development is thus another object of this invention.

Natural intra-species differentiation becomes apparent in the early stages of forest development and is indicated, in part, by differences in the heights of the members of the same species as illustrated in FIG. 2. This FIGURE is a block diagram illustrating the number of trees of differing heights in a 2-milliacre test plot at the site described in Examples 1 through 5, infra. This plot, being one of numerous such plots in the site described in the examples, contained 198 trees of which 50 percent were Douglas fir, 9.6 percent were Grand fir, and 40.4 percent were Western hemlock. All of these conifers were approximately 6 years old. Broadleaf varieties, which accounted for approximately 30 to about 40 percent of the ground cover, are not represented in FIG. 2. This FIGURE illustrates a substantial distribution of tree heights even at this stage of forest development. Some members of the same species are hardier and have grown faster than others.

The tolerance of different members of the same species for adverse conditions is also reflected in their tolerance for the foliar application of these solutions. Thus these methods can be used to eliminate a substantial part of the original growth during the early stages of forest development. As a consequence, the competition from weaker trees is reduced at an earlier stage, while the growth rate of stronger trees is increased by fertilization.

As a practical matter these forced thinning methods can be practiced at any time prior to the complete development of a mature forest stand of the preferred conifers, i.e., within 20–25 years of growth, when the population comprises two or more species of different tolerance to foliar application of these solutions. However, for the reasons described above, greater advantage is generally obtained by treatment within about the first 10 years of growth, preferably within 5, or even within 3 years of growth. The best results are obtained during the earliest stages of forest development, i.e., shortly after the preferred seedlings have become established. This generally occurs within one year of planting or natural reseeding. Discrimination between the weaker and stronger members of the same species can be produced in any of these periods, but is best accomplished within the first year of growth.

Somewhat different factors are involved in discriminating between broadleaf trees and members of the pine family. The great majority of broadleaf trees initially grow much faster than do Pinaceae. This point is illustrated graphically by reference to FIG. 1 which is a schematic illustration of the sigmoid growth curves for Douglas fir and vine maple trees comparing tree height to age. This illustration is a rough approximation of the sigmoid growth curves for the average members of a hypothetical vine maple and Douglas fir population. These species were selected as representative of their respective classes, e.g., pine family and broadleaf. Thus the growth curves roughly represent the relative growth rates of the two generic classes.

From this comparison it is apparent that the broadleafs initially gain height much faster than do the conifer seedlings. For instance, after only 3 years, the vine maple population on the average has reached a height of approximately 15 feet compared to a height of only about 3 to 4 feet for the Douglas fir. As a consequence, the broadleaf trees have a decided competitive advantage in the early growth stages and can actually crowd or starve out and kill conifer seedlings in their immediate vicinity. It is obviously desirable to avoid this occurrence by eliminating competition by the broadleaf trees as early as possible.

The crossover point between the sigmoid growth curves of the Pinaceae and broadleaf trees generally occurs within about 3 to about 10 years of growth. As illustrated in FIG. 1, the crossover of the curves for the population selected for this comparison occurs at about 6 years, at which time the trees have reached heights of about 20 feet. After this point competition for light and space gradually turns in advantage of the taller conifers. Thus the elimination of competion by broadleaf varieties is not as critical after this growth stage. Nevertheless, some advantage can be gained by eliminating the broadleafs even after the crossover of the sigmoid growth curves since the broadleaf trees do continue to compete for water and nutrients.

The unpreferred trees include: (1) any of the numerous broadleaf trees, brush and weeds known to generally populate forested areas; (2) one or more Pinaceae species having lower tolerance to the nitrogenous solutions than do the preferred species; and (3) the weaker members of the preferred species having lower tolerance than do the hardier members of the same species. Illustrative of the broadleaf varieties are the maple genus including numerous species of maples, the birch genus including the common birch and alders, the genus Populus including poplars, the beech genus including numerous varieties of oaks and other species. Low lying broadleafs include numerous varieties of weeds, vines, and bushes such as ferns, i.e., the class Filicineae, running or climbing vines such as wild grapes, so-called arrowroot plants of the genus Maranto, wild flowering plants such as thistles and goldenrod and the numerous wild shrubs generally referred to as brush and characterized as woody plants having several permanent stems rather than a single trunk.

The selective elimination of broadleafs is preferably accomplished with solution of sufficient nitrogen concentration and in sufficient dosages to completely eliminate all broadleaf trees. However, any degree of thinning has a beneficial effect. Thus nitrogen concentration and dosage level should be adjusted to eliminate at least about 50 percent and preferably at least about 70 percent of the competing, unpreferred broadleaf trees. Broadleafs usually constitute about 0.5 and generally between about 1 and 50 percent of the total tree population on a number basis in the initial growth stages, i.e., before crossover of the conifer and broadleaf sigmoid growth curves. The population density of broadleafs and Pinaceae can obviously vary over a wide range without negating the benefits of this invention. It is equally apparent, however, that the greatest advantage is realized with higher relative broadleaf populations.

This can be accomplished without substantial damage to any significant part of the conifer population. It is possible to thin the broadleaf varieties while eliminating less than 10 percent of the preferred conifers. Obviously, more severe conditions are required to eliminate a significant percentage of the conifer population, e.g., one or more competing species of the pine family or a substantial percentage of the members of the same species. In these cases dosage levels should be sufficiently mild to allow for the survival of at least about 20 and preferably at least about 30 percent of the members of the preferred species. Thus intra-species thinning is generally accomplished with conditions sufficient to eliminate about 20 to about 80, preferably between about 30 and about 70 percent of the members of that species.

All areas will not support the same population density nor will trees of a given species grow at the same rate or to the same size in all areas due to the differing ability of those areas to support tree growth. Area productivity is a function of several factors including rainfall, other climatic conditions, soil nutrients level, etc. These differences are reflected by the site classification system used by the Forest Service and commercial timber growers. Growing areas are generally characterized as site classes having designations 1 through 5, class 1 being the most favorable growing area. It is thus desirable to eliminate a greater percentage of the original trees assuming the same degree of initial overstocking in the poorer site classes.

Thinning can be accomplished without completely killing the unpreferred species of class members. Burn levels of as low as 50 percent deter the growth of undesired trees sufficiently to give the stronger trees a competitive advantage. The percentage of foliar burn is easily determined by visual inspection approximately 1–2 weeks after treatment and measuring the percentage of foliage dessicated. More dramatic results are achieved at higher burn levels, e.g., at least 60 or 70 percent on the unpreferred trees. Broadleaf foliage can be completely desiccated at severity levels that cause only nominal damage to the Pinaceae species.

These solutions have two apparently opposing effects — fertilization and foliage burning or desiccation. The fertilizing effect generally predominates at levels of foliar burn of 30 percent or less. The growth deterrent effect usually prevails for up to about one growing season at dosage levels sufficient to cause significantly more than about 30 percent foliage loss. Secondly, the foliage loss by weaker species or trees is noticeably greater than is the case with the hardier trees. Thus a burn level of 50 percent can be obtained on the broadleaf species with nitrogen concentrations and dosage levels that will cause substantially less burn on the desired conifers, e.g., on the order of 20 percent or less. The fertilizer effect will predominate on the conifers while the deterrent effect of foliage loss will predominate on the broadleaf trees even though that species may not be completely killed. This degree of differentiation is sufficient to give the conifers a growth advantage during the period in which the effect of foliage loss predominates on the broadleaf trees, i.e., for about 1 to 3 growing seasons depending on burn severity, even though the broadleafs are not completely killed.

Suitable nitrogen compounds are those which act as plant fertilizers at higher concentrations and dosage levels but which are also sufficiently strong foliage desiccants. Illustrative of these are urea, ammonia, nitrates of ammonium, calcium and potassium, ammonium sulfate and combinations of these. The solutions should contain amounts of these compounds corresponding to at least about 12.5 weight percent, usually between about 12.5 and about 45 weight percent, preferably between about 15 and about 32 weight percent elemental nitrogen. More concentrated solutions are preferred when applied by aerial spraying.

The maximum nitrogen concentration obtainable without precipitation of nitrogen salts or ammonia evolution is a function of compound type and temperature. Compositions containing 45 weight percent elemental nitrogen cannot be produced from all of these compounds. Such solutions must contain substantial amounts of ammonia. Particularly preferred solutions contain combinations of urea and ammonium nitrate due to their availability, solution stability and the high nitrogen levels obtainable, e.g., 15 to about 32 weight percent. The eutectic combination of urea and ammonium nitrate containing 44.3 weight percent ammonium nitrate and 35.4 weight percent urea corresponding to 32 weight percent elemental nitrogen is particularly preferred.

The extent of foliage burning is a function of several variables including total nitrogen dosage, e.g., pounds of nitrogen per acre, the identity of the nitrogen source or sources, solution concentration, the generic tree class (broadleaf vs. conifers), and intra-species genetic differences. Conifers are much stronger in this respect than are the broadleaf trees. Secondly, the several nitrogen compounds desiccate foliage to different degrees. For instance, the foliar burn on Douglas firs treated with 160 pounds per acre of a urea solution containing 20 weight percent nitrogen was only about one-half that observed with similar applications of ammonium nitrate. Thus the burning tendency of ammonium nitrate on Douglas fir was approximately twice as great as that of urea.

These differences can be readily evaluated for any particular application by a simple testing procedure in which solutions of various concentrations of several different compounds are applied to different test plots at different total dosage levels. For instance, separate solutions of urea, ammonium nitrate, ammonium sulfate, etc., and combinations of these can be formulated at different nitrogen concentrations, e.g., 15, 20, 25 and 30 weight percent elemental nitrogen, and applied to separate test plots at several dosage levels between 20 and 600 pounds of nitrogen per acre varying in 40-pound per acre increments. A study of this nature would allow correlation for the given tree population and growing conditions of the several variables governing foliar desiccation. The investigator can then select the particular combination of nitrogen compound, solution concentration and dosage level most appropriate for his purposes. The objective of the study would, of course, be to determine which combination of variables provides the greatest degree of elimination of the unpreferred trees while not causing intolerable foliage loss to the preferred species.

Testing procedures of this type can involve field application to test plots of trees of the desired age or greenhouse tests on seedling trees. Due to the severity of these tests, the use of seedlings between about 3 and about 12 months old in greenhouse tests is preferred. Different age seedlings can of course be employed although trees in this age group are suitable.

An illustrative approach for greenhouse or small plot testing is the so-called log sprayer well known to the art. In the use of this apparatus the tree seedlings are aligned in a plurality of rows, e.g., up to 100 rows or more. The sprayer usually comprises a spray pipe parallel with the rows and extending over the samples to be sprayed and travels across all of the sample trees sequentially from one row to the next. The sprayer is supplied from a solution reservoir that initially contains a predetermined amount of a solution of known composition. As the solution is consumed it is simultaneously diluted with water at a predetermined rate so that the concentration of the applied solution varies sequentially from one row to the next. Thus, the full range of solution concentrations and dosage levels can be covered from one extreme to the other.

The initial solution concentration can be fixed at a level which will kill all trees in the population while only a few or none of the trees will be killed by the most dilute solution at the end of the test. Observation of the total population after a period of time sufficient to exhibit the affects of spraying, e.g., about 2 to 3 weeks, will enable the investigator to closely approximate the conditions of solution concentration and dosage level most desirable for his purpose.

The tree population employed in this procedure is determined by the type of differentiation desired. A combination of broadleafs and conifers can be used if discrimination between these two classes is the primary objective. For that matter, the same population can be used to evaluate discrimination between broadleafs and conifers and also to determine treatment conditions necessary to eliminate a certain percentage of conifers of the same species. However, a more accurate evaluation of differentiation between members of the same species might be accomplished by employing a tree population comprising only trees of that species. The same procedure can be used to establish conditions necessary to discriminate between different species of the family Pinaceae by employing a sample tree population including the several tree species.

Obviously numerous other testing procedures could be employed. For instance, solution concentration could be maintained at the same value throughout the test while varying spraying rate. This approach would allow treatment of all sample trees with a solution of the same composition at different dosage levels. Similarly, parallel tests can be run on a plurality of sample groups using solutions of different compounds, mixtures of compounds or different concentrations to evaluate these variables.

The determination of conditions suitable for discrimination between broadleafs or conifers or between members of the same conifer species is straightforward. Broadleaf species as a class are more susceptible to damage than are conifers as a class. Similarly, there are always weaker members of the same species present in any given population which will be preferentially eliminated. Hence, it might appear that these methods are of only limited utility for discriminating between different conifers. It would seem reasonable to assume that any two conifer species would exhibit the same reaction, relative to each other, regardless of solution compositions or method conditions. In other words, it would appear that a species which is more tolerant under one set of conditions would be more tolerant under all conditions.

We have discovered that this is not the case. For instance, Douglas firs are much more susceptible to foliage desiccation with urea solutions than are hemlock or Grand fir. In contrast, however, hemlocks are significantly more susceptible to damage by ammonium nitrate or combinations of ammonium nitrate and urea than are Douglas firs. Grand firs react to approximately the same extent to ammonium nitrate solutions as do Douglas firs.

Thus, by changing solution composition one can change the selectivity of the procedure depending upon the primary objective in a given situation. For instance, hemlock can be selectively eliminated from a dominant Douglas fir stand with ammonium nitrate or combinations of ammonium nitrate and urea, whereas Douglas fir growth rate relative to hemlock can be attenuated with urea solutions. The exact solution composition most suitable for a given application in this respect, i.e., discrimination between different conifer species and other method conditions required for that purpose, can be easily determined by the parallel screening test procedures described above.

As a general rule, significant differentiation between broadleaf and Pinaceae trees can be obtained at dosage levels of at least about 30 pounds per acre. Complete elimination of all broadleaf species can be accomplished at dosage levels of about 50 pounds nirogen per acre or greater. The foliage loss by members of the pine family at the minimum dosage levels is nominal at most. Preferably the total application rate should not be so high as to cause more than 30 percent foliage loss of the preferred conifers. The dosage level causing this degree of conifer foliage loss can be easily determined by the testing procedure described above. As a general rule, however, the confiers can be treated at relatively high total nitrogen levels, i.e., up to 400 pounds of nitrogen per acre, without unacceptable foliage loss by stronger trees.

A similar technique can be used to determine the conditions that should be used to differentiate the stronger and less hardy members of the same species. For instance, a population of Douglas fir, loblolly pine or the like could be treated at nitrogen dosage levels sufficient to burn about 30 to about 50 percent of the foliage of the total population on the average. Some trees, the less hardy members of the species, would be burned to a much greater extent than will the hardier members of the class. Thus the stronger trees on the average might suffer only 20 to 30 percent foliage loss while the less hardy trees might lose 80 percent or all of their foliage at the same dosage level. The dosage level required for this effect will depend on the several variables discussed above such as the nitrogen source, solution concentration, tree species, site class, climate, etc. As a general rule, however, dosage levels employed to distinguish between the weaker and the stronger members of the same species of Pinaceae will range between about 150 and 600, preferably between about 200 and about 400, pounds of nitrogen per acre.

The results of these tests will usually become apparent fairly rapidly, i.e., within several weeks, generally within about 2 weeks. The extent of foliar burning can be readily determined visually by inspection after 2 weeks or, if desired, over a period of time, e.g., at 2, 4 and 6 weeks, etc. The degree of burn, i.e., burn index, can be characterized by any method that allows the investigator to evaluate the extent of foliar damage on the different species or members.

For instance, the foliar burn index can be graded on a scale of 1 to 10: the minimum value of 1 indicating that less than 10 percent of the total foliage is damaged, i.e., spotted, brown or missing. The maximum value of 10 is assigned if 91 to 100 percent of the total foliage is damaged. Intermediate values are assigned proportionately for intermediate damage levels, i.e., a burn index of 7 would correspond to a damage level of about 61 to 70 percent indicated by foliage browning or loss.

Conversely, the fertilization effect can be graded by evaluating the degree of foliage greening occasioned by these methods. An indication of the presence or absence of foliage greening can be obtained by comparing the original foliage color to a series of standard color plates. Comparison of these plates to the foliage after treatment will then indicate whether or not the treatment has produced a color change. Color change or index can be graded on a scale of 1 to 5 as follows: (1) no apparent change; (2) possible but questionable change; (3) probable change; (4) most probable change; and (5) certain change or increased greening. Other scales and indications can of course be employed.

These results will generally enable the investigator to determine offhand at least qualitatively the presence or absence of desiccation or greening effects. However, it may be desirable to evaluate the results by a more sophisticated procedure such as statistical regression analysis. Such procedures are well known and enable evaluation of the relationships between the observed data and tree species, nitrogen compound type, dosage level, solution concentration and the like. They also afford an indication of the reliability of results, i.e., the correlation coefficients which relate to the certainty with which the particular result can be predicted.

Having these results, the investigator can then select the nitrogen compounds, solution concentrations and dosage levels that will best serve his purpose by selecting the values for each variable which will produce the desired degree of species differentiation and fertilization.

The solutions can be applied by hand spraying or mechanical spraying from land vehicles or can be aerially applied by helicopter or other aircraft. The amount of solution applied will generally be determined by the desired solution concentration and the total dosage level. These application rates usually correspond to about 15 to about 200, preferably about 25 to about 100 gallons of solution per acre. A second consideration involves the aount of solution required to sufficiently cover the foliage and distribute the compounds without substantial drainage from the foliage to the forest floor. Such drainage is preferably avoided for several reasons. Little benefit is achieved by applying fertilizer to the forest floor and such application results in contamination of ground water and adjacent rivers and streams.

The solutions are preferably applied annually although more frequent applications such as semi-annual or quarterly treatments can be used. Applications are preferably made shortly before or during the active growing season, e.g., in the early or late spring so that the best advantage is achieved most readily from the fertilizer effect on the preferred species. Similarly, the differentiation effect will be more readily apparent during the active growing season, particularly in the case of broadleaf species due to the higher foliage levels during that period.

In addition to the above-described nitrogen compounds, these solutions can also contain other plant nutrients including micronutrients, insecticides, selective herbicides and surfactants. The use of surfactants is preferred to adequately wet the foliage surface. Micronutrients are well known in the art and include iron, cobalt, molybdenum, manganese, copper, boron, zinc and magnesium. They are preferably incorporated in the form of water soluble salts at concentrations corresponding to about 0.01 to about 5, preferably about 0.5 to about 2.5 weight percent of the metal. Suitable compounds include salts such as the sulfates, nitrates, phosphates, halides and the like, although the halides are less preferred in some cases due to their phytotoxicity. Any of the numerous well known chelating agents can be used to assure solubility of the micronutrient metal compounds.

Macronutrients such as potassium, phosphorus and sulfur can be added in conventional forms such as the soluble potassium salts or sulfur-containing salts and acids, e.g., potassium nitrate, potassium sulfate, sulfurous acid, ammonium or potassium orthophosphates, pyrophosphates, tripolyphosphates, and the like. Concentrations of these materials usually correspond to about 2 to about 20, preferably about 2.5 to about 10 weight percent determined as $K_2O$, $P_2O_5$ and $SO_3$.

The solutions can also include iron nutrients in forms which can be assimilated by the plants. However, we have discovered that many iron compounds reduce the foliage burning tendency of these solutions. Accordingly, the total nitrogen dosage level should be increased substantially, e.g., by about 20 percent, when using iron-containing solutions in order to obtain the same degree of differentiation that would be realized with otherwise identical solutions in the absence of the iron compounds. The exact degree of burning attenuation introduced by the iron compounds for a given tree population can be readily determined by the parallel screening procedures described herein.

The compounds and solutions described in the U.S. Pat. Nos. 3,679,377 and 3,753,675 are illustrative of materials suitable for use in this embodiment.

These solutions contain from 0.05 to 20 weight percent iron in the ferric oxidation state and are prepared by the addition of metallic iron or a ferrous halide, nitrate or $C_1$ to $C_5$ carboxylate to an ammonium nitrate solution having from 5 to about 70 weight percent ammonium nitrate and a pH from 1 to about 3 at autooxidation conditions comprising a time and temperature sufficient to cause evolution of nitrogenous gases from the solution and to impart to said solution a red coloration. The resulting solution contains a highly soluble complex of iron which is believed to be present as a $\mu$-dihydroxo diferrate anion in complex association with a total of eight additional ligands, at least two of which are sulfato, halo or nitroso and the balance being aquo or hydroxo.

The complexes can be recovered from the ammonium nitrate solution used in their preparation by extraction with acetone and concentration of teh acetone extract until the following ammonium salts pecipitate:

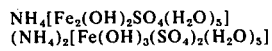

$$NH_4[Fe_2(OH)_2SO_4(H_2O)_5]$$
$$(NH_4)_2[Fe(OH)_3(SO_4)_2(H_2O)_5]$$

These salts can then be dissolved in the nitrogenous solution. Alternatively, urea or excess nitrate can be added to the a-monium nitrate-iron complex solution to obtain mixed solutions.

Even distribution and rapid solution assimilation by the plant foliage is promoted by minor amounts of conventional surfactants, e.g., about 0.1 to about 2.5, preferably about 0.25 to about 1.0 weight percent. These surfactants improve distribution of the solutions over the foilage and assist in absorption. They can include cationic, anionic and nonionic surfactants and combinations of these. Numerous surfactants are known to the art such as the fatty amines, alkarylamines, fatty amides, quatermary alkyl and aryl ammonium salts and hydrates, quaternary ammonium bases of fatty amines of disubstituted diamines, fatty acid sulfonates, sulfonated fatty amides, amides of amino sulfonic acids, alkylaryl sulfonates and the like. Illustrative nonionic surfactants include polyethylene oxide condensates with hydrophobic groups having reactive hydrogens. These hydrophobic groups can have from about 8 to 25 carbons and from about 2 to 15 molecular weights of the hydrophilic group. The hydrophobic groups can be selected from a variety of organic compounds having 1 or more reactive hydrogens including fatty alkyl or alkenyl alcohols, fatty acids, amines and amides, esterified hexitans or alkenyl phenols. The hydrophilic groups can be ethylene oxide moieties or groups such as ethylene chlorohydrin or polyethylene gylcol. Still other illustrative surfactants include the organic substituted ammonium salts of sulfodicarboxylic acids that are reacted with various hydrophobic groups such as fatty amides having 12 to 18 carbons to produce half amides in the manner described in U.S. Pat. No. 2,976,290. Other materials of this type are described in U.S. Pat. Nos. 2,976,211, 3,080,280 and 2,975,208.

Selective herbicides can also be included to provide better control of specific species. Illustrative of these are chlorophenoxyalkenoic acids, esters and salts of these acids such as 2,4-dichlorophenoxyacetic acid, 2,4,5-trichlorophenoxyacetic acid, etc.; the alkali metal salts or esters of such acids with $C_1$ to $C_8$ alkanols, glycols, glycol monoethers and the like such as sodium-2,4-dichlorophenoxyacetate, octyl-2,4-dichlorophenoxyacetate, and the like. Yet another class of selective herbicides includes the carbamates such as the $C_1$ to $C_5$ alkyl-N-phenyl carbamates, alkyl thiocarbamates such as isopropyl-N-phenylcarbamate, ethyl-N-chlorophenyl carbamate, and the like. Urea derivatives having selective phytotoxicity include the N,N'-substituted ureas having phenyl, chlorphenyl, $C_1$–$C_5$ alkyl, alkoxy and chloroalkyl or chloronorbornyl substituents. Illustrative compounds include 3-phenyl-1,1-dimethyl urea, 2-(3,4-dichlorophenyl)-1,n-butyl-1-methyl urea, etc. Selectively phytotoxic amides include the $C_2$–$C_6$ alkyl, chloroalkyl, phenylalkyl, naphthaalkyl, and alkenyl amides containing N-phenyl, N-alkyl, N-chlorophenyl and N-alkenyl substituents.

Examples of suitable insecticides include the chlorinated hydrocarbons such as DDT, bis(p-chlorphenyl)-trichloroethane and related compounds, e.g., methoxychlor, Dilan, bis(p-chlorophenoxy)methane, bis(p-chlorphenyl)ethanol, chlorobenzilate, p-chlorphenyl phenyl sulfone, etc. Other chlorinated hydrocarbons include benzene hexachloride, Lindane, Chlordane, Aldrin, Dieldrin, Heptachlor, Toxaphene, etc.

The organic phosphorus insecticides can also be used including tetraethyl pyrophosphate, tetraethyl dithiopyrophosphate, octamethyl pyrophosphoramide, Parathion, Para-oxon, Methyl Parathion, Chlorothion, o-ethyl-o-p-nitrophenyl benzenethiophosphate, Diazinon, Malathion, Demeton, etc.

Insecticidal carbamates include ferric dimethyl dithiocarbamate, trimethylphenyl methyl carbamate, 4-(dimethylamino)-m-tolyl methylcarbamate, 4-(methylthio)-3,5-xylylmethylcarbamate, 4-benzothienyl-N-methylcarbamate, s-ethyl dipropylthiocarbamate, 2,3-quinoxalinedithiol cyclic trithiocarbamate, 1-naphthyl-N-methylcarbamate, 2-isopropoxyphenyl N-methylcarbamate, etc.

Various fungicides include: chloranil, 2,3-dichloro-1,4-naphthoquinone, pentachlorophenol, metallic dialkyl diethiocarbamates such as zinc or ferric dimethyldithiocarbamate, disodium ethylene bisdithiocarbamate, manganese ethylene bis-dithiocarbamate, etc., captan, colloidal sulfur, lime sulfur, ammonium polysulfide, etc.

The naturally occurring insecticides can also be used such as the various pyrethrums, e.g., pyrethrin I, cinerain I, pyrethrin II, cinerin II, jasmolin II, etc., and synthetically prepared and related insecticides such as allethrin, furethrin, cyclethrin, barthrin, dimethrin, super pynamin, etc. Rotenone, dequelin, dihydrorotenone, dihydrodequelin, etc., can also be used.

The aforementioned pesticides can be admixed with any of the aforementioned fertilizer solutions in proportions such that the final aqueous material applied will provide from 0.1 to about 5 pounds per acre of the pesticide. A preferred dosage is from 0.5 to about 3 pounds per acre.

EXAMPLES 1 through 8

These eight examples illustrate differentiation between broadleafs and conifers and between different conifer species. The test site was a heavily overstocked replanted location in the State of Washington containing conifers ranging from 3 to about 6 feet tall with a population density of about 30,000 trees per acre comprising primarily Douglas fir with smaller percentages of hemlocks and Grand fir. Approximately 30 to 40 percent of the ground surface was covered with broadleaf varieties including numerous species of brush and trees consisting mostly of vine maple and alder ranging in height from seedlings to in excess of 6 feet. The soil in the test site was a poor gravelly loam, 18 to 36 inches in depth on compacted glacial till having an approximate 8 percent slope with North aspect. This site was divided into 100 separate test plots each having an area of 2 milliacres with each test plot being separated by untreated guard plots to prevent overspraying.

This very small plot size necessitated the use of handheld sprayers with fine nozzles. Due to the small tree and plot sizes only very minor amounts of concentrates were required when applied as such. For instance, the volume of concentrated ammonium nitrate-urea (32 weight percent N) required to obtain a per acre dosage of 160 pounds nitrogen was only 8 ml per tree. The lower per acre dosage levels required even lower volume rates of the concentrate. It was exceedingly difficult and time consuming to obtain even distribution of these concentrates at these volume rates even with hand-held sprayers.

Uniform coverage could be more easily obtained by applying the nitrogen compounds as dilute solutions. Before proceeding in this manner, however, it was necessary to determine that the effects of both the dilute and concentrated solutions were identical when applied at the same per acre nitrogen dosage. In other words, it was necessary to establish the validity of the premise that the response of conifers and broadleafs to these solutions was a function of total nitrogen applied rather than concentration. This determination was made in the following manner.

Eight individual Douglas fir trees about 3 feet tall were selected from the population described above and were treated with 32-0-0 urea-ammonium nitrate solutions utilizing a hand atomizer. Uniform distribution was obtained by spraying each tree on all sides from top to bottom taking into account the total amount of solution applied in each instance.

The eight test trees were divided into two groups of four. The first group was treated with 1, 2, 4 and 8 ml of 32-0-0 concentrate, respectively. At the stocking density of the test area, 30,000 trees per acre (30 trees per milliacre), 1 ml of 32-0-0 corresponded to a total dosage of 20 pounds of nitrogen per acre. The second group was treated with the same amounts of 32-0 -0 diluted with water to a total volume of 200 ml. Previous studies on trees of the same size from the same population established that uniform 250 ml per tree application rates were required to produce any noticeable runoff. Reducing the volume to 200 ml and taking care to assure uniformity provided a sufficient safety factor to avoid runoff and nitrogen loss.

Foilage damage, the degree of spotting and browning, was determined by close visual inspection 24 hours after application. The results of these determinations are given in the following Table.

Table 1

| Ex. No. | Concentration,[1] wt. % N | Urea-Ammonium Nitrate lbs. N/at[2] | Total Vol., ml. | Burn[3] Index |
|---|---|---|---|---|
| 1 | 32 | 20 | 1 | 1 |
| 2 | 32 | 40 | 2 | 1 |
| 3 | 32 | 80 | 4 | 2 |
| 4 | 32 | 160 | 8 | 4 |
| 5 | 0.16 | 20 | 200 | 1 |
| 6 | 0.32 | 40 | 200 | 1 |
| 7 | 0.64 | 80 | 200 | 2 |
| 8 | 1.28 | 160 | 200 | 4 |
| Blank | — | — | — | 1 |

[1]Each solution contained one drop Emcol H3A surfactant.
[2]Based on established stocking density of 30,000 trees per acre and test dosage per tree.
[3]Burn index of 1 is insignificant above background (Blank).

These results established that foliage desiccation is governed by the total nitrogen dosage rather than concentration. We therefore concluded that results representative of the trees' response to concentrates could be obtained with solutions which had been diluted sufficiently to allow uniform distribution with available spraying equipment.

EXAMPLES 9–15

The plots described in Examples 1–8 were treated at 4 rates of 20, 40, 80, and 160 pounds of nitrogen per acre with solutions prepared from the materials listed in the following Table. Each treatment was replicated four times.

Table 2

| Ex. No. | Description |
|---|---|
| 9 | Water + 0.5 % surfactant |
| 10 | Mixed mono- and di-ammonium ortho-phosphate solution (10 wt. % N) |
| 11 | Ammonium nitrate with soluble iron sulfate complex (18 wt. % N) |
| 12 | Ammonium nitrate solution (20 wt. % N) |
| 13 | Mixed urea and ammonium nitrate solution (32 wt. % N) |
| 14 | Urea solution (12 wt. % N) |
| 15 | Urea prills (46 wt. % N) |

Each of the lower three rates of application were applied in 80 gallons of solution per acre. The final dosage of 160 pounds of nitrogen per acre was applied in 160 gallons of solution per acre to obtain adequate distribution. As illustrated in Examples 1–8, this spray volume was adequate to provide good coverage without any substantial runoff. The resulting concentrations are given in Table 3.

Table 3

| Dosage, lbs. N/acre | Total Volume, Gal/at | Concentration,[1] Wt. % N |
|---|---|---|
| 20 | 80 | 2.8 |
| 40 | 80 | 5.6 |
| 80 | 80 | 11.1 |
| 160 | 160 | 11.1 |

[1]These values were the same for all solutes tested.

Each plot was evaluated visually for foliar burn and color change at 2, 6 and 10 weeks after treatment. Foilar burn was graded on a scale of 1 to 10 and greening response on a scale of 1 to 5. Approximately 100,000 separate observations or data points were obtained during this investigation. These data were statistically evaluated by standard regression analysis to determine the relationships between three species, solution composition, dosage level and other variables.

The surfactant (Ex. 9) and dry urea prills (Ex.No. 15) caused no foliar burn. Conifer desiccation with ammonium phosphate (Ex.No. 10) above background was so minimal, even at the maximum dosage level, that a reliable correlation could not be obtained. The results obtained with the urea and ammonium nitrate solutions correlated well with the expression.

$$B = C_1 d + K_1$$

wherein:
$B$ = foliar burn rating on a scale of 0–10
$C_1$ = regression coefficient
$d$ = fertilizer dosage, pounds N/acre
$K_1$ = constant or background burn rating.
$K_1$, the background burn rating, was determined by observation of separate untreated plots and was approximately 1 in each instance. Regression coefficients, $C_1$, representing the degree of variance of foliage desiccation as a function of dosage level, were significant in all cases with the exception of ammonium phosphate. These values are given in Table 4. This Table also lists values for relative foliage desiccation using the foliar burn of the Douglas fir as a standard (1.000).

Table 4

| Ex. No. | Compound | Specie[1] | $C^{(2)}$ | RFD[3] |
|---|---|---|---|---|
| 10 | Urea | ASP | 0.0147 | — |
| | | DF | 0.0147 | 1.000 |
| | | HL | 0.0047 | 0.320 |
| | | GF | 0.0094 | 0.640 |
| 11 | Urea/$NH_4NO_3$ | ASP | 0.0325 | — |
| | | DF | 0.0250 | 1.000 |
| | | HL | 0.0300 | 1.200 |
| | | GF | 0.0247 | 0.988 |
| | | BL | 1.000 | Indeterminate |
| 12 | $NH_4NO_3$ | ASP | 0.0275 | — |
| | | DF | 0.0247 | 1.000 |
| | | HL | 0.0294 | 1.190 |
| | | GF | 0.0266 | 1.077 |
| | | BL | 1.000 | Indeterminate |
| 13 | $NH_4NO_3$ + Fe | ASP | 0.0166 | — |
| | | DF | 0.0159 | 1.000 |
| | | HL | 0.0134 | 0.843 |
| | | GF | 0.0122 | 0.7673 |
| | | BL | 1.000 | Indeterminate |
| 14 | $(NH_4)_3PO_4$ | ASP | 0.0034 | — |
| | | DF | 0.0034 | 1.000 |
| | | HL | 0.000 | — |
| | | GF | 0.0003 | 0.088 |

[1]ASP = All species of conifer; DF = Douglas fir; HL = hemlock; GF - Grand fir; BL - broadleaf.
[2]Regression coefficient
[3]Relative foliar desiccation; DF = 1.000

All of the broadleaf trees, brush and weeds were destroyed by the urea solution (Ex. No. 10) at dosage levels above 40 pounds of nitrogen per acre. The 20 pound per acre dosage level of this solution also inflicted significant damage on the broadleafs. Accordingly, the correlation coefficient for the broadleafs was very close to unity. Broadleaf desiccation data was not sufficient to afford an adequate basis for correlation in Example No. 14. However, in Examples 11 through 13, all broadleaf species were completely killed even at the minimum dosage level, resulting in a correlation coefficient to 1.000. Obviously, the relative foliage desiccation factor compared to the conifers was indeterminate from these results.

These results also illustrate that these methods can be used to differentiate between different conifer species. For instance, the hemlock and Grand firs were substantially more tolerant to the urea solution in Example 10 than were the Douglas fir trees. Conversely, the Douglas fir and Grand fir were substantially more tolerant to ammonium nitrate in Examples 11 and 12 than were the hemlocks. Accordingly, ammonium nitrate selectively retards hemlock growth rate while urea can be used to selectively retard the growth rate of Douglas fir trees relative to hemlock and Grand fir.

The maximum conifer burn level was only about 60 percent. In other words, the maximum burn level achieved was sufficient to destroy only 60 percent of the conifer foliage. Subsequent measurements of the tree growth revealed that even at the maximum burn level the conifer growth rate in the following growing season averaged over all tree sizes was not significantly retarded. Thus, higher dosage levels, e.g., on the order of 400 pounds per acre or more would be required to eliminate a significant percentage of the conifer population.

EXAMPLES 16 THROUGH 21

While the maximum dosage levels (160 pounds per acre) of the most active nitrogen solutions were not sufficient to kill the weaker conifers outright, they did have an effect sufficient to illustrate differentiation between weaker and hardier members of the same species. Intra-species differentiation was determined by measuring the height of every conifer tree in all the test plots prior to application and again after two growing seasons. This data allowed determination of growth rate. The results were then divided into two classifications — growth rates for trees having final heights of less than 105 centimeters and for trees taller than 135 centimeters. These values were compared to the growth rates for identical trees in the same height classes in untreated plots, i.e., plots sprayed with the 0.5 weight percent surfactant solution. The results obtained at the 160 pounds nitrogen per acre levels are summarized in Table 5.

Table 5

| | | Percent Growth Increase[1] | |
|---|---|---|---|
| Ex. No. | Solution | Less Than 105 cm.[2] | Greater Than 135 cm.[2] |
| 16 | urea | 5.7 | 10.6 |
| 17 | urea-$NH_4NO_3$ | 6.0 | 15.3 |
| 18 | $NH_4NO_3$ | 2.4 | 11.2 |
| 19 | $NH_4NO_3$ + Fe | 9.3 | 15.0 |
| 20 | ammonium phosphates | 14.6 | 15.9 |
| 21 | $H_2O$ + 0.5 % surfactant | [38.0][3] | [36.5][3] |

[1]Relative to initial height and comparable untreaed trees.
[2]Final tree height.
[3]Percent growth based on final height.

The growth rate results are reported as the "percent growth increase" for the two tree height classifications. These values were determined by actual measurements of the tree height for each height class and comparison of the growth rates over the two-year test to the growth rates of trees treated with the water-surfactant combination (Example 21). The results of Example 21 are reported as percent growth rather than percent growth increase. Thus the untreated trees in the 105 centimeter class grew 38 percent while those of heights greater than 135 centimeters grew 36.5 percent.

Solutions of urea, ammonium nitrate and combinations of these were employed in Examples 16 through 19. In each instance the percent growth increase attributable to the nitrogenous solutions was substantially greater with trees having heights greater than 135 centimeters. In fact, the response for these trees, as compared to the smaller trees, was generally at least twice as great. Even this degree of differentiation would be sufficient to give the stronger, taller trees an additional growth advantage thereby promoting selective thining. Even greater advantage could be obtained at higher dosage levels.

The ammonium phosphate solution of Example 20 promoted little or no intra-species differentiation as indicated by a substantially comparable percent growth increase values for the two height classifications. This result might be expected in view of the observed low burning tendency of ammonium phosphates. It does lend support to the prediction that this type of differentiation is the consequence of foilage desiccation.

EXAMPLE 22

This test site was located at Shively Creek, approximately 7 miles southeast of Canyonville, Orgeon. The test plots were located on a northeast aspect in the headwaters of Shively Creek at an elevation of 2500 to 2850 feet having slopes ranging from 20 to 45 percent. The soils are characterized as developing from a highly fractured metamorphic shale, well drained, and overlain by a dark brown clay loam having a red, gravelly clay subsoil, the combination being approximately 40 inches deep and containing 35 to 50 percent highly weathered shale fragments. The plots, which had been pre-commercially thinned, contained 140 to 225 20-year-old Douglas fir per acre having an average d.b.h. (diameter at breast height) of 1.5 inches. These trees shielded approximately 50 percent of the ground surface. Extensive deciduous growth included madrone, chinkipin, red alder and willow.

Circular plots 1/5 acre in area were sprayed by helicopter with 150 pounds per acre of an aqueous solution of urea and ammonium nitrate containing 32 weight percent nitrogen. At this level, 93 percent of the Douglas fir had some needle injury as evidenced by tip browning. However, only 4 percent of the conifers had as much as 30 percent foilage burn. Thus these treatments occasioned little or no permanent damage as a consequence of foliage decissation. However, all broadleaf species which were contacted by the aerial spray, i.e., which were not shielded by conifers, were completely killed.

We claim:

1. The method of simultaneously fertilizing and selectively thinning forests comprising preferred commercial timber trees of the family Pinaceae and unpreferred forest plants having a lower tolerance than said preferred trees to foliar application of the aqueous nitrogenous fertilizer hereinafter defined, which method includes the steps of reducing the growth rate of said unpreferred plants relative to said preferred trees by applying to the foilage of all of said trees and plants an aqueous nitrogenous solution of a water-soluble nitrogen source selected from the group consisting of urea; ammonia; nitrates of ammonia, calcium and potassium; ammonium sulfates; and combinations thereof, in an amount corresponding to at least about 12.5 weight percent elemental nitrogen at a total elemental nitrogen dosage level sufficient to reduce the growth rate of said unpreferred plants.

2. The method of claim 1 wherein said solution of said nitrogen source is aplied to said trees and plants at a total nitrogen dosage level sufficient to kill at least 50 percent of said unpreferred plants and less than 10 percent of said preferred trees.

3. The method of claim 1 wherein said forest comprises trees selected from the group consisting of the species *Abies, Cedrus, Larix, Picea, Pinus, Pseudotsuga, Tsuga*, and combinations thereof and broadleaf plants, and said nitrogenous solution is applied to the foliage of all of said trees and plants at a dosage level sufficient to kill at least about 70 percent of said broadleaf plants.

4. The method of claim 1 wherein said forest comprises trees of Pinaceae family and broadleaf trees, and said nitrogenous solution is aerially sprayed on the foilage of all of said trees at a rate of at least about 30 pounds of elemental nitrogen per acre sufficient to kill at least about 70 percent of said broadleaf trees.

5. The method of claim 4 wherein said preferred trees are common commercial timber trees selected from the group consisting of Grand fir, Red fir, Pony fir, hemlock spruce, cedar, loblolly pine, Ponderosa pine, lodgepole pine, white pine and combinations thereof, and said nitrogenous solutions is applied to the foliage of all of said trees at a rate corresponding to at least about 50 pounds of elemental nitrogen per acre of said forest.

6. The method of claim 5 wherein said broadleaf trees comprise primarily species selected from the group consisting of maple, birch, beech and combinations thereof.

7. The method of claim 1 wherein said forest trees are less than about 5 years old.

8. The method of claim 6 wherein the majority of said broadleaf trees are taller than the majority of said preferred trees, and at least 90 percent of said trees are less than about 3 years old.

9. The method of claim 1 wherein said unpreferred forest plants include the weaker 20 to about 80 percent of said trees of the family Pinaceae and said nitrogenous solution is aerially applied to the foliage of all of said trees and plants at a rate of at least about 300 pounds of nitrogen per acre sufficient to kill about 20 to about 80 percent of said trees of the family Pinaceae.

10. The method of claim 9 wherein said nitrogen source is selected from the group consisting of urea and ammonium nitrate and combinations thereof and the concentration of said nitrogen source in said aqueous nitrogenous fertilizer corresponds to an elemental nitrogen content of about 15 to about 32 weight percent.

11. The method of claim 1 wherein said unpreferred plants include at least the smallest 20 percent of said trees of the family Pinaceae, said preferred trees comprise at least the tallest 20 percent of said trees of the family Pinaceae and are selected from the group consisting of Grand fir, Red fir, Pony fir, hemlock, spruce, cedar, loblolly pine, Pondersoa pine, lodgepole pine and white pine, and said nitrogenous solution contains at least about 15 weight percent nitrogen and is aerially aplied to the foliage of all of said trees and plants at a rate corresponding to at least about 300 pounds of elemental nitrogen per acre sufficient to accelerate the growth rate of said preferred trees and at least deter the growth rate of said unpreferred trees relative to said preferred trees.

* * * * *